United States Patent [19]
Foley et al.

[11] Patent Number: 6,096,172
[45] Date of Patent: Aug. 1, 2000

[54] METHOD OF BONDING BIO-MOLECULES TO A TEST SITE

[75] Inventors: Barbara Foley, Phoenix; Natalia Briones, Mesa, both of Ariz.

[73] Assignee: Motorola, Inc., Schaumburg, Ill.

[21] Appl. No.: 09/174,606

[22] Filed: Oct. 19, 1998

[51] Int. Cl.$^7$ .............................. C07C 1/00; C12N 11/00
[52] U.S. Cl. ....................... 204/157.15; 435/174
[58] Field of Search ........................ 204/157.15; 435/174

[56] References Cited

U.S. PATENT DOCUMENTS

| | | | |
|---|---|---|---|
| 4,894,339 | 1/1990 | Hanazato et al. | 435/182 |
| 5,372,914 | 12/1994 | Naito et al. | 430/296 |
| 5,919,712 | 7/1999 | Herron et al. | 436/518 |

OTHER PUBLICATIONS

The American College Dictionary, p. 1150, 1970 *no month available.

*Primary Examiner*—Kathryn Gorgos
*Assistant Examiner*—Edna Wong
*Attorney, Agent, or Firm*—Eugene A. Parsons; William E. Koch

[57] ABSTRACT

A method of bonding bio-molecules to a test site including providing a substrate having a test site defined on a surface thereof, providing a solution containing a plurality of probe molecules and bonding material, directing light from a light source onto the test site so as to cause the bonding material to bond the probe molecules to the test site.

5 Claims, 2 Drawing Sheets

METHOD OF BONDING BIO-MOLECULES TO A TEST SITE

FIELD OF THE INVENTION

This invention relates to fabrication of bio-molecule analyzers.

More particularly, the present invention relates to methods of bonding, i.e. fixing or attaching physically but not necessarily chemically, bio-molecules to test sites.

BACKGROUND OF THE INVENTION

Identification of molecular structure has become very important in many industries. In particular, biological molecules such as nucleic acids and proteins are analyzed to form the basis of clinical diagnostic assays. The procedures utilized often involve large numbers of repetitive steps which consume large amounts of time. With the advent of large projects such as the human genome project, faster and less complex techniques are required.

Simpler and quicker analysis of molecules has been provided by the development of devices often referred to as bio chips, which are arrays of test sites formed on a substrate. Each of the plurality of test sites includes probes therein to bond with target molecules from samples applied to the device. The binding of a molecule to a probe is noted, thereby identifying the molecule.

While increasing the speed and efficiency of analyzing samples, the arrays of test sites must still immobilize specific bio-molecules on a solid surface to act as probes. Conventional bonding of probe molecules to the test sites includes polymerization of monomers attached to the probe molecule. While effective, the bond can be tenuous. Thus a new and novel method of bonding is desired, which provides robust and uniform deposition of the bio-molecule probes.

It would be highly advantageous, therefore, to remedy the foregoing and other deficiencies inherent in the prior art.

Accordingly, it is an object of the present invention to provide a new and improved bonding method.

Another object of the present invention is to provide a method of bonding probe molecules to test sites which is robust and uniform.

SUMMARY OF THE INVENTION

Briefly, to achieve the desired objects of the instant invention, in accordance with a preferred embodiment thereof, provided is a method of bonding bio-molecules to a test site including providing a substrate having a test site defined on a surface thereof, providing a solution containing a plurality of probe molecules and bonding material, directing light from a light source onto the test site so as to cause the bonding material to bond the probe molecules to the test site.

In a specific method of bonding, the bonding material includes a binder which cross-links under the influence of the light, capturing and retaining the bio-molecules.

A further specific method of bonding includes providing a test site having a metal base, directing the light onto the metal base so as to heat the metal base, and providing a bonding material, bonded to the bio-molecules, which melts in response to the heat of the metal base and adheres to the test site.

BRIEF DESCRIPTION OF THE DRAWINGS

The foregoing and further and more specific objects and advantages of the instant invention will become readily apparent to those skilled in the art from the following detailed description of preferred embodiments thereof taken in conjunction with the drawings in which.

DETAILED DESCRIPTION OF THE PREFERRED EMBODIMENTS

Figure 1:
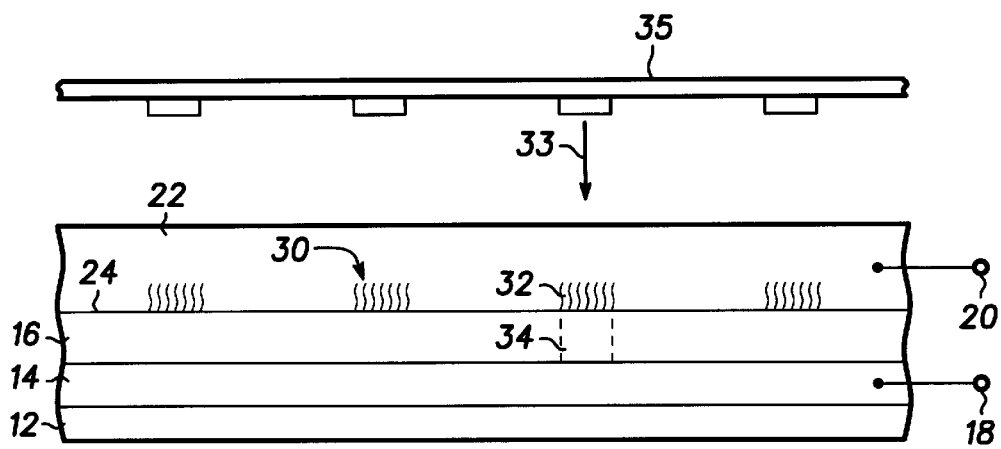
FIG. 1 is a sectional view of a bio-molecule analyzer according to the present invention.

Turning now to the drawings in which like reference characters indicate corresponding elements throughout the several views, attention is first directed to FIG. 1 which illustrates a bio-molecule analyzer generally designated 10. Bio-molecule analyzer 10 includes a substrate 12 preferably fabricated of silicon, glass, plastic, etc., a thin conductive layer 14 formed on substrate 12, and a photoconductive layer 16 formed on thin conductive layer 14. Thin conductive layer 14 can be any conductive material such as gold, platinum etc., and can be indium tin oxide (ITO) or other optically transparent conductors for reasons which will become apparent from the subsequent description. Photoconductive layer 16 is a material such as amorphous silicon, CdS, CdSe, various photoconductive polymers, etc. which becomes conductive when subjected to light.

Still referring to FIG. 1, a lead 18 is coupled to conductive layer 14 and a lead 20 is coupled to a solution 22 positioned in electrical contact with a surface 24 of photoconductive layer 16 opposite to conductive layer 14. While not specifically shown, it will be understood that solution 22 is in electrical contact only with surface 24 and not with conductive layer 14. A potential is applied across leads 18 and 20 and thus between solution 22 and conductive layer 14.

Still referring to FIG. 1, a beam or beams of light 33 are directed through a portion 34 of photoconductive layer 16 defining a test site 30 (preferably one test site for each beam). In this embodiment, test sites 30 are formed into an array, with each test site 30 being an area of surface 24 substantially coextensive with a corresponding portion 34. The beam or beams of light 33 complete an electrical circuit between conductive layer 14 and solution 22 through portion 34 of photoconductive layer 16. This is accomplished by beam of light 33 temporarily converting portion 34 of photoconductive layer 16 to a conducting medium.

Solution 22 contains ionic probe molecule to be bound to test sites 30. By completing the circuit, the ionic probe molecules in solution 22 are attracted to and concentrate proximate surface 24 at a selected one or ones of test sites 30. It will be understood that any method of controllably illuminating a selected portion 34 of photoconductive layer 16 can be used, such as a masked light source, the use of a laser or diode array 35 or similar device instead of or in combination with a mask which permits passage of light in only the desired locations. Array 35 can be a one dimensional or two dimensional array of light sources which are individually addressable, i.e. one or more light sources can be activated as desired.

The array of test sites 30 (micro-locations) defined on surface 24 have groups of probes 32 coupled thereto. Each test site 30 contains a plurality of probes 32 which are capable of binding to specific molecular structures. The molecular structure can comprise, for example, bio-molecules such as polynucleotides, protein, DNA, RNA, enzymes, antibodies, antigens, etc. In the case of DNA or RNA testing, probes 32 can comprise, for example, oligonucleotides. All probes 32 at a given test site 30 are identical. Probes in respective test sites differ in sequence for simultaneous detection of a plurality of different target molecules within a single array. Each test site 30 is individually addressable by array 35 to provide the ability to attract ionic probe molecules from solution 22 to selected test site(s) 30 in order to fabricate an array of test sites each for detecting different molecules or sequences.

Figure 2:
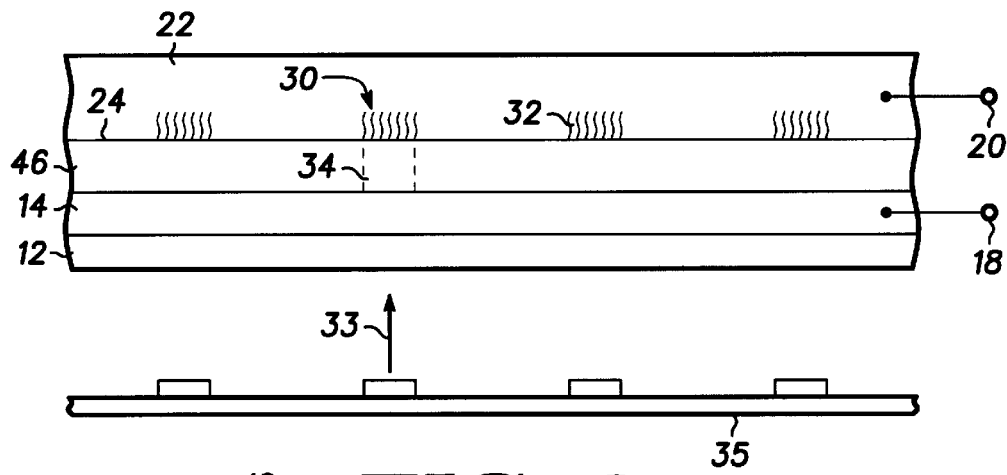
FIG. 2 is a sectional view illustrating another embodiment of a bio-molecule analyzer according to the present invention.

In the previous description, light 33 is directed at photoconductive layer 16 through solution 22. With reference to FIG. 2, the same elements are illustrated, but light 33 is directed through substrate 12 and thin conductive layer 14. In this case, substrate 12 must be formed of a material transparent to light 33 such as glass, plastic, etc., and thin conductive layer 14 must be a transparent conductor such as indium tin oxide (ITO), various thin metals or other optically transparent materials. It will be understood that when the term transparent is used throughout the text, it refers to a material's ability to transmit light being used to transform photoconductive layer 16.

A specific process of fabricating a bio-molecule analyzer (e.g. analyzer 10) includes providing a first solution, containing a plurality of first probe molecules, in electrical contact with the plurality of test sites 30. An electrical potential is applied between the first solution and the layer of electrically conductive material 14 by means of leads 18 and 20. A beam of light 33 is directed through a first portion 34 of the photoconductive layer 16 to complete an electrical circuit between the layer of electrically conductive material 14 and the first solution through the first portion 34 of the photoconductive layer 16 and a first test site 30 of the array of test sites. Completing the electrical circuit causes first probe molecules in the first solution to be attracted to a first test site 30.

After being attracted to first test site 30, a method of bonding bio-molecules according to the present invention is employed. The first solution contains bonding material along with the first probe molecules. Beam of light 33 from the light source is contemporaneously directed onto the first test site so as to cause the bonding material to bond the first probe molecules to the first test site by entrapment of the probes in the bonding material which will be cross-linked by the presence of the light.

The circuit is then broken by deactivating the light source and the first solution is removed leaving a test site with a plurality of identical probes bound thereto.

The fabrication process continues by providing a second solution, containing a plurality of second probe molecules, in electrical contact with the plurality of test sites 30. An electrical potential is applied between the second solution and the layer of electrically conductive material 14 by means of leads 18 and 20. A beam of light 33 is directed through a second portion 34 of the photoconductive layer 16 to complete an electrical circuit between the layer of electrically conductive material 14 and the second solution through the second portion 34 of the photoconductive layer 16 and a second test site 30 of the array of test sites. Completing the electrical circuit causes second probe molecules in the second solution to be attracted to a second test site 30 where they are bound as described above and as described in greater detail below.

This process is repeated as many times as needed to produce a bio-molecule analyzer having a desired number or array of different test sites each with different probe molecules. In this fashion, an analyzer having a one or two dimensional array of test sites can be easily fashioned which is less labor intensive, quicker to process and includes the ability to build very small test sites.

Figure 3:
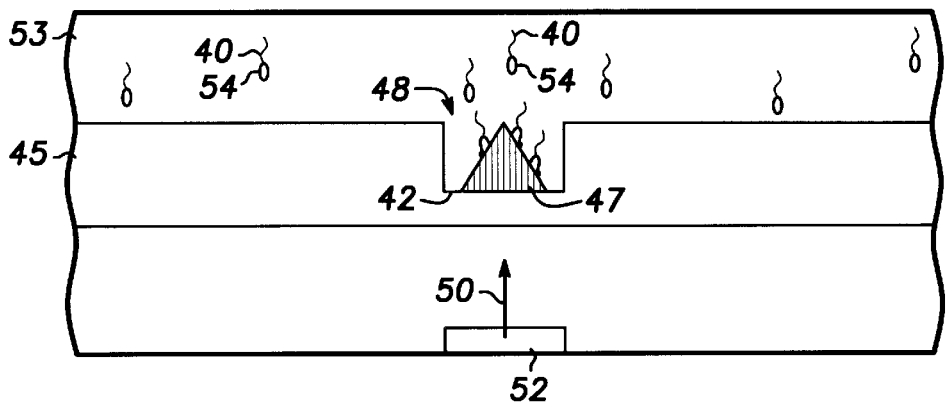
FIG. 3 is a greatly enlarged sectional view illustrating a method of bonding bio-molecules to a test site according to the present invention.

Turning now to FIG. 3, illustrated is a specific method of bonding probe molecules 40 to a test site 42 according to the present invention. The method includes providing a substrate 45 having test site 42 defined on a surface thereof. In this specific embodiment, test site 42 is defined by a depression 48 formed in the surface of substrate 45 and includes a metal base 47 formed therein. Metal base 47 can be formed in any convention manner such as depositing by small melting metal tip. A beam of light 50 from a light source 52 is directed onto metal base 47 so as to heat metal base 47. A solution 53 includes bonding material 54 coupled to bio-molecules 40. Bonding material 54 melts in response to the heat of metal base 47 and adheres to test site 42 in depression 48 and to metal base 47. Any material which can be bonded to the probe molecules and which will melt at the temperatures generated can be employed. An example of a bonding material is polystyrene which has been chemically modified, as will be understood by those skilled in the art, to perform the bonding or entrapment features. It should be understood that while metal base 47 is shown as being conical in shape, other shapes (e.g. single shapes or plurality of shapes which can include cones, blobs, droplets, pads, etc.) are anticipated, with the conical shape providing the largest surface area and providing the most efficient shape for heat conduction.

Figure 4:
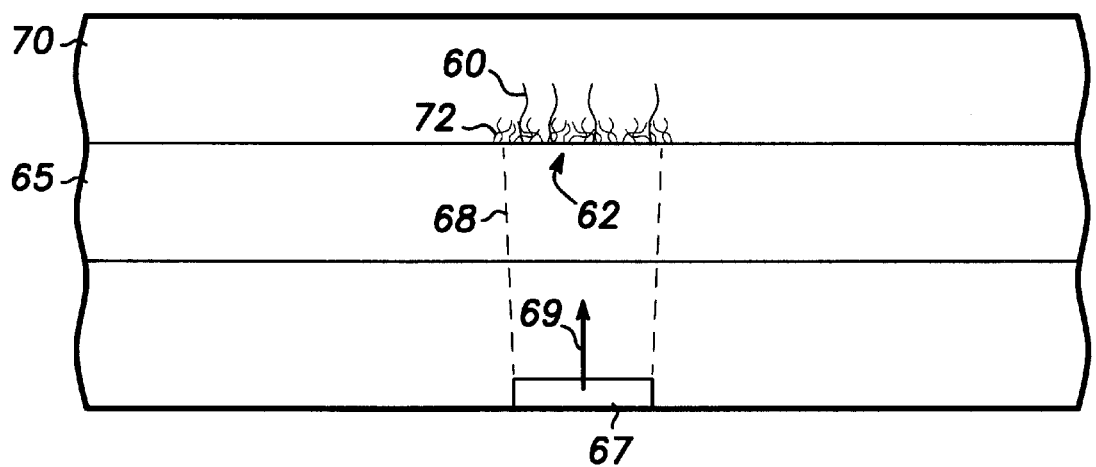
FIG. 4 is a greatly enlarged sectional view illustrating another method of bonding bio-molecules to a test site according to the present invention.

Referring now to FIG. 4 illustrated is another method of bonding probe molecules 60 to a test site 62 according to the present invention. The method includes providing a substrate 65 having test site 62 defined on a surface thereof. In this specific embodiment, test site 62 is defined by a light source 67 as illustrated by broken lines 68. A beam of light 69 from light source 67 is directed onto test site 62. A solution 70 includes bonding material 72 which crosslinks under the influence of beam of light 69, capturing and retaining probe molecules 60. In this specific embodiment, the bonding material is polyacrylamide. However, one skilled in the art will understand that other bonding materials may be employed which cross-link in the presence of light.

While a specific analyzing system utilizing electrical circuitry is disclosed above, it will be understood that this method can be used to fabricate any bio analyzer in which probe molecules are bonded, i.e. fixed or attached, to a test site.

Thus provided is a method of bonding, fixing, or attaching probe molecules to test sites which is robust and uniformly distributes probe molecules.

Various modifications and changes to the embodiments herein chosen for purposes of illustration will readily occur to those skilled in the art. Other modifications and variations may be made by those skilled in the art without departing from the scope of the invention as defined by the following claims.

Having fully described and disclosed the present invention and preferred embodiments thereof in such clear and concise terms as to enable those skilled in the art to understand and practice same, the invention claimed is:

1. A method of bonding DNA molecules to a test site comprising the steps of:

provideing a substrate having a test site defined on a surface thereof;

providing a solution containing a plurality of DNA probe molecules and bonding material;

providing a light source; and directing light from the light source onto the test site so as to cause the bonding material to bond the DNA probe molecules to the test site.

2. A method as claimed in claim 1 wherein the bonding material includes a binder which cross-links under the influence of the light, capturing and retaining the DNA molecules.

3. A method as claimed in claim 2 wherein the binder includes polyacrylamide.

4. A method of bonding DNA molecules to a plurality of test sites comprising the steps of:

providing a substrate having a plurality of test sites defined on a surface thereof;

providing a first solution containing a plurality of first DNA probe molecules and bonding material;

providing a light source; and directing light from the light source onto a first test site of the plurality of test sites so as to cause the bonding material to bond the first DNA probe molecules to the first test site;

providing a second solution containing a plurality of second DNA probe molecules and bonding material; and directing light from the light source onto a second test site of the plurality of test sites so as to cause the bonding material to bond the second DNA probe molecules to the second test site.

5. A method as claimed in claim 4 wherein the bonding material includes a binder which cross-links under the influence of the light, capturing and retaining the DNA molecules.

\* \* \* \* \*